US010653845B2

(12) United States Patent
Butts et al.

(10) Patent No.: US 10,653,845 B2
(45) Date of Patent: May 19, 2020

(54) COVERINGS FOR SYRINGE PLUNGER TIPS AND METHODS RELATED THERETO (71) Applicant: Merit Medical Systems, Inc., South Jordan, UT (US)

(72) Inventors: David Butts, Riverton, UT (US); Richard Jenkins, Bluffdale, UT (US); Gregory R. McArthur, Sandy, UT (US); John Hall, North Salt Lake, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 15/410,305

(22) Filed: Jan. 19, 2017

(65) Prior Publication Data

US 2017/0209648 A1 Jul. 27, 2017

Related U.S. Application Data (60) Provisional application No. 62/281,279, filed on Jan. 21, 2016.

(51) Int. Cl.
*A61M 5/315* (2006.01)
*A61L 31/04* (2006.01)
*A61L 31/14* (2006.01)

(52) U.S. Cl.
CPC ....... *A61M 5/31513* (2013.01); *A61L 31/041* (2013.01); *A61L 31/048* (2013.01); (Continued)

(58) Field of Classification Search
CPC ................................................ A61M 5/31513
See application file for complete search history.

(56) References Cited

U.S. PATENT DOCUMENTS 4,439,184 A 3/1984 Wheeler
4,500,310 A 2/1985 Christinger
(Continued)

FOREIGN PATENT DOCUMENTS

EP 0338671 10/1989
EP 0375778 7/1990
WO 2004044464 5/2004

OTHER PUBLICATIONS

International Search Report and Written Opinion dated May 22, 2017 for PCT/US2017/014043.
(Continued)

*Primary Examiner* — Nathan R Price
*Assistant Examiner* — Dung T Ulsh
(74) *Attorney, Agent, or Firm* — Stoel Rives LLP (57) ABSTRACT Coverings for syringe plunger tips, as well as syringes and syringe components including such coverings, are disclosed. A material of the covering may have at least one different material property than a material of the plunger tip. The coverings may provide a reduced coefficient of friction between the covering and a surface of the syringe relative to the coefficient of friction between the plunger tip and the syringe surface. The coverings may also isolate a substance loaded in the syringe from the plunger tip. Methods for manufacturing a syringe assembly including such coverings, as well as methods for isolating a substance in a syringe from a syringe component, are also disclosed.

9 Claims, 6 Drawing Sheets (52) U.S. Cl.
CPC ...... *A61L 31/14* (2013.01); *A61M 2205/0222* (2013.01); *A61M 2205/0238* (2013.01); *A61M 2207/00* (2013.01)

(56) References Cited

U.S. PATENT DOCUMENTS

| | | | |
|---|---|---|---|
| 4,997,423 A | 3/1991 | Okuda | |
| 5,009,646 A | 4/1991 | Sudo | |
| 5,314,416 A * | 5/1994 | Lewis | A61M 5/31513 600/576 |
| 5,397,313 A * | 3/1995 | Gross | A61M 5/31513 604/218 |
| 5,411,488 A | 5/1995 | Pagay et al. | |
| 5,735,825 A | 4/1998 | Stevens et al. | |
| 7,186,242 B2 | 3/2007 | Gyure et al. | |
| 7,927,315 B2 | 4/2011 | Sudo et al. | |
| 8,475,415 B2 * | 7/2013 | Schiller | A61M 5/31513 604/222 |
| 8,740,856 B2 | 6/2014 | Quinn et al. | |
| 9,592,346 B2 | 3/2017 | Quinn et al. | |
| 10,183,118 B2 | 1/2019 | Quinn et al. | |
| 2001/0004466 A1 | 6/2001 | Heinz et al. | |
| 2002/0198500 A1 | 12/2002 | Leung | |
| 2004/0122376 A1 | 1/2004 | Gyure et al. | |
| 2004/0138612 A1 * | 7/2004 | Shermer | A61M 5/142 604/93.01 |
| 2005/0137533 A1 * | 6/2005 | Sudo | A61M 5/31511 604/218 |
| 2006/0178643 A1 | 8/2006 | Sudo et al. | |
| 2007/0219508 A1 * | 9/2007 | Bisegna | A61M 5/31513 604/218 |
| 2011/0034882 A1 * | 2/2011 | Quinn | A61M 5/31511 604/218 |
| 2011/0178475 A1 | 7/2011 | Tanaka et al. | |
| 2012/0136298 A1 * | 5/2012 | Bendix | A61M 5/2448 604/89 |
| 2014/0031764 A1 * | 1/2014 | Abe | A61M 5/31513 604/221 |
| 2014/0062036 A1 | 3/2014 | Maeda et al. | |
| 2014/0207081 A1 | 7/2014 | Quinn et al. | |
| 2015/0018800 A1 | 1/2015 | Reb et al. | |
| 2016/0243305 A1 * | 8/2016 | Nakamura | A61M 5/2033 |
| 2017/0312177 A1 * | 11/2017 | Bhargava | A61J 1/2093 |
| 2019/0142433 A1 | 5/2019 | Hopkinson et al. | |

OTHER PUBLICATIONS

Office Action dated Jul. 11, 2018 for U.S. Appl. No. 15/410,364.
European Search Report dated Aug. 26, 2019 for EP17741885.2.
Office Action dated Jul. 8, 2019 for U.S. Appl. No. 15/410,364.
Office Action dated Jan. 31, 2019 for U.S. Appl. No. 15/410,364.
Office Action dated Jan. 8, 2020 for U.S. Appl. No. 15/410,364.

* cited by examiner

COVERINGS FOR SYRINGE PLUNGER TIPS AND METHODS RELATED THERETO

RELATED APPLICATIONS

This application claims priority to U.S. Provisional Application No. 62/281,279 titled, "COVERINGS FOR SYRINGE PLUNGER TIPS AND METHODS RELATED THERETO" and filed on Jan. 21, 2016 which is hereby incorporated by reference in its entirety.

TECHNICAL FIELD

The present disclosure relates to the field of medical devices. More specifically, the present disclosure relates to a syringe having a syringe plunger and a syringe plunger tip. Even more specifically, the present disclosure relates to various coverings for syringe plunger tips and methods related thereto.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings, in which:

DETAILED DESCRIPTION

Coverings for syringe plunger tips, as well as syringes and syringe components having such coverings, are disclosed herein. In some embodiments, a covering is disposed on at least a portion of an external surface of a syringe plunger tip. The covering may comprise a material that is different than the material of the plunger tip. The material properties of the covering and the plunger tip may differ in at least one material property, as described more fully below. For example, the covering may comprise a material with a lower coefficient of friction when in contact with the interior surface of a syringe barrel than the material of the plunger tip. Further, in some embodiments, the plunger tip may compress to provide a sealing force between the plunger tip and covering and the interior surface of a syringe barrel.

The covering may further comprise a material that isolates, for example by physical and/or chemical separation, a plunger tip from a substance loaded into a reservoir defined by an interior surface of a syringe barrel. Again, this isolation may be due to prevention of physical contact between the plunger tip and the substance. Further, the covering may be substantially impermeable to migration of chemical components of the plunger tip across the covering.

In some embodiments, the covering comprises one or more polymeric materials. Syringe tip coverings within the scope of this disclosure may comprise polymeric materials including, but not limited to, linear low-density polyethylene (LLDPE), high-density polyethylene (HDPE), expanded polytetrafluoroethylene (ePTFE), polytetrafluoroethylene (PTFE), or a composite of any of these materials. Such coverings may facilitate, for example, controlled sliding of a syringe plunger tip along the length of an interior surface of a syringe barrel. Additionally or alternatively, such coverings may prevent a substance loaded within a syringe barrel from being contaminated by syringe components.

In some embodiments, a covering may prevent contact between a silicone plunger tip and, for example, a substance containing polyvinyl alcohol (PVA) within the syringe barrel. In other embodiments, a covering may prevent contact between a silicone plunger tip and a substance containing gelatin foam (examples include SurgiFoam™ from Ethicon or Gelfoam™ from Pfizer) within the syringe barrel. In some instances, silicone plunger tips may be incompatible with use of PVA or gelatin foam. In some instances, for example, silicone material from the plunger tip or silicone lubrication within the syringe barrel may tend to coat or otherwise adhere to the PVA or gelatin foam if these components are in contact. This may, in turn, interfere with hydration of PVA or gelatin foam particles thus causing them to agglomerate. Thus, the coverings provided herein may be impermeable or demonstrate low permeability to silicone to prevent such contamination. As used herein, silicone refers broadly to polymeric compounds that consist of silicon-oxygen backbone chains ( . . . —Si—O—Si—O— . . . )$_n$ (e.g., compounds containing one or more siloxane groups).

Methods for manufacturing a syringe assembly including a covering for a syringe plunger tip are also provided by the present disclosure. In some embodiments, the methods comprise coupling a covering to a syringe plunger tip, wherein the plunger tip comprises a first material and the covering comprises a second material, and wherein at least one material property of the first material differs from at least one material property of the second material. The covering may be coupled to the plunger tip through a number of different processes, including, for example, depositing the covering onto the plunger tip (e.g., by electrospinning, electrospraying, rotational spinning, spraying, or deposition (i.e., desublimation)), stretching, shrinking, and/or wrapping the covering onto the plunger tip, adhering the covering to the plunger tip with an adhesive, applying a heat-shrink covering onto the plunger tip, or coupling the covering to the plunger tip with a friction fit, e.g., with ridges or detents on the covering that engage the plunger tip to hold the covering in place. In some embodiments, the method may further comprise loading a substance comprising PVA or gelatin foam into a reservoir defined by an interior surface of a syringe barrel, wherein said reservoir is configured to receive the plunger tip. In some embodiments, the first material comprises silicone and the second material comprises LLDPE, HDPE, PTFE, or ePTFE.

Methods for isolating PVA or gelatin foam from a syringe component (e.g., a syringe plunger tip) comprising silicone are also provided herein. In some embodiments, the methods comprise coupling a covering to a plunger tip, wherein the plunger tip comprises a first material and the covering comprises a second material, and wherein at least one material property of the first material differs from at least one material property of the second material. The methods may further comprise disposing the syringe plunger tip within a reservoir defined by an interior surface of a syringe barrel and loading the reservoir with a substance comprising PVA or gelatin foam, wherein the covering isolates the syringe plunger tip from the substance by preventing physical contact between the syringe plunger tip and the substance. In some embodiments, the covering may be coupled to the plunger tip through a number of different processes, including, for example, depositing the covering onto the plunger tip (e.g., by electrospinning, electrospraying, rotational spinning, deposition (i.e., desublimation), or spraying), stretching and/or wrapping the covering onto the plunger tip, adhering the covering to the plunger tip with an adhesive, applying a heat-shrink covering onto the plunger tip, or coupling the covering to the plunger tip with a friction fit, e.g., with ridges or detents on the covering that engage the plunger tip to hold the covering in place.

It will be readily understood with the aid of the present disclosure that the components of the embodiments, as generally described and illustrated in the figures herein could be arranged and designed in a variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The terms "proximal" and "distal" refer to opposite ends of a medical device. As used herein, the proximal end of a medical device is the end nearest a practitioner during use, while the distal end is the opposite end. For example, the proximal end of a standard syringe refers to the end associated with the plunger handle while the distal end corresponds to the outlet.

The term "material property" refers to any property or characteristic of a substance comprising components described herein. For example, material properties may include, but are not limited to, a material's chemical makeup (e.g., materials that contain silicon versus those that do not), a material's coefficient of friction as measured with another material or surface, a material's permeability, and other physical, chemical, mechanical, structural, electrical or other properties.

Figure 1A:
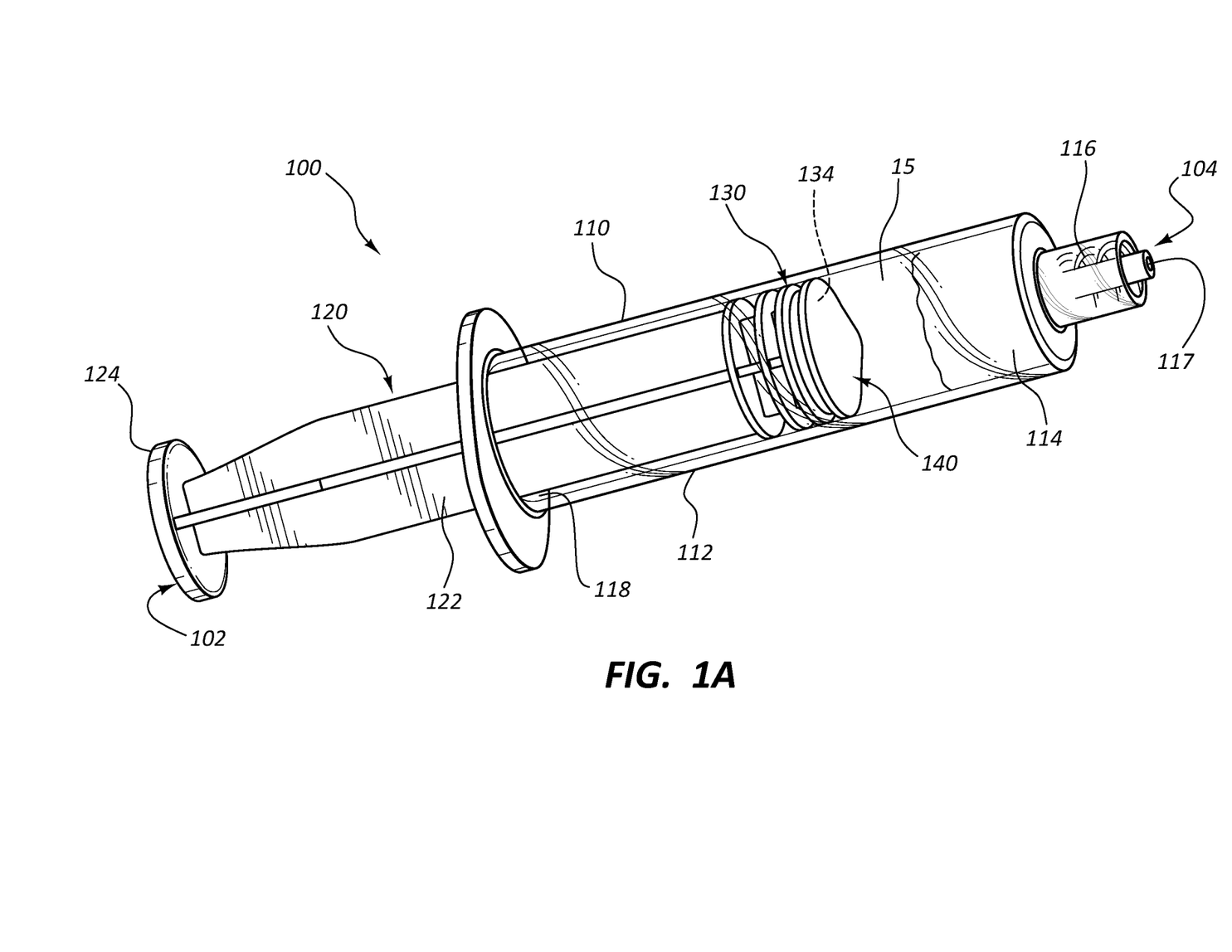
FIG. 1A illustrates a perspective view of an embodiment of a syringe assembly according to the present disclosure.
Figure 1B:
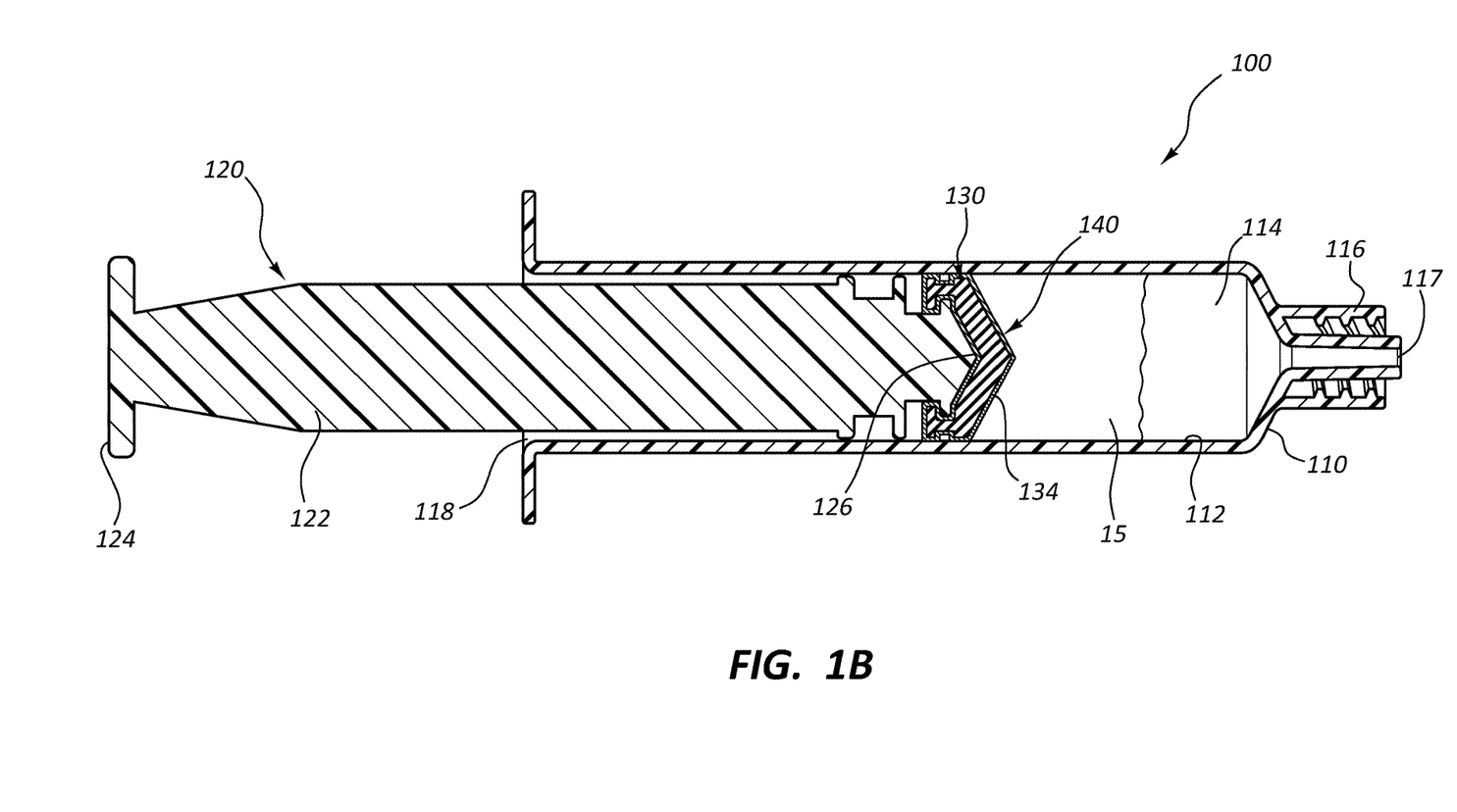
FIG. 1B illustrates a side cross-sectional view of the syringe assembly of FIG. 1A.
Figure 1C:
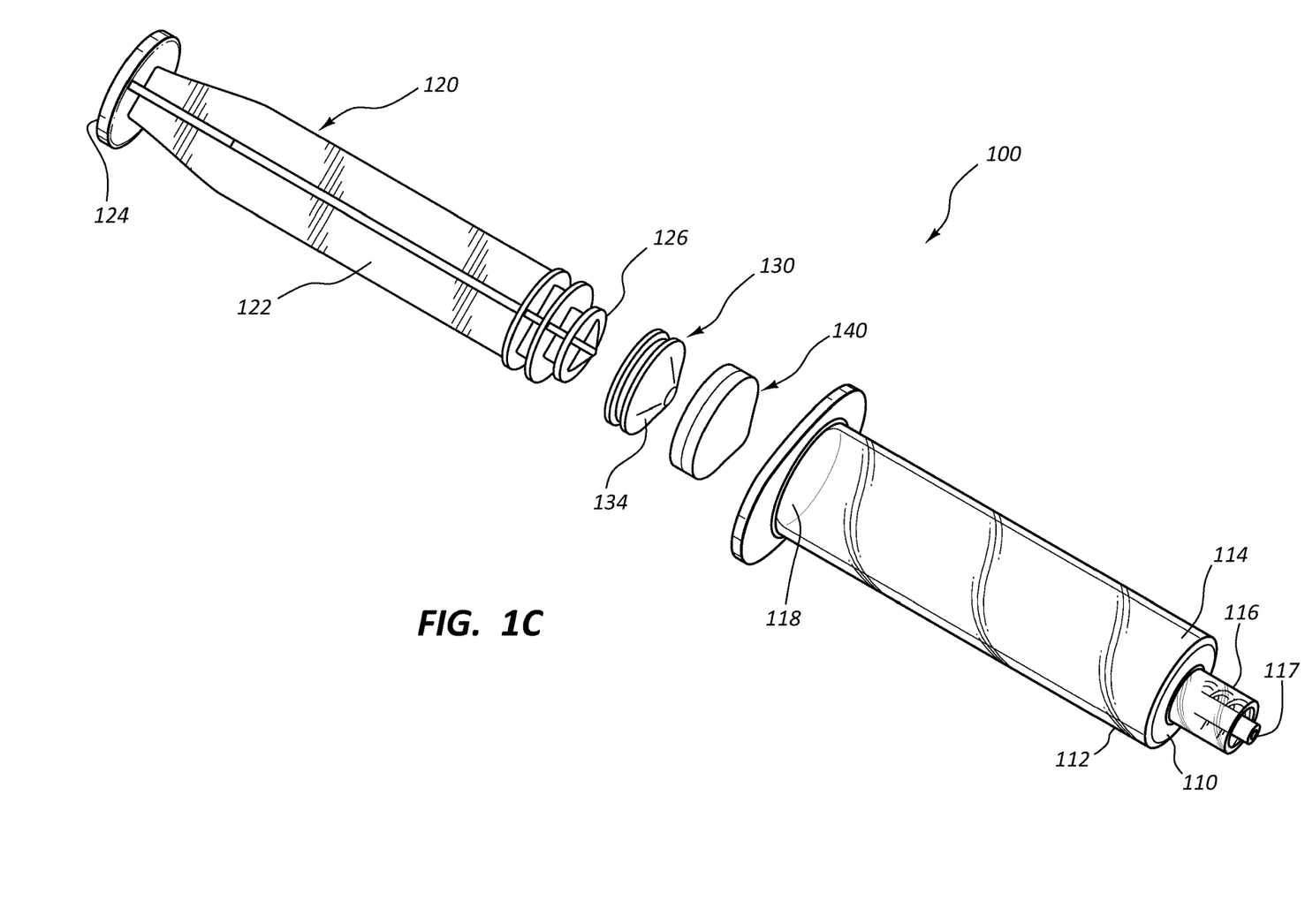
FIG. 1C illustrates an exploded view of the syringe assembly of FIG. 1A.

FIGS. 1A, 1B, and 1C are, respectively, a perspective view, a cross-sectional view, and an exploded view of one embodiment of a syringe assembly 100 according to the present disclosure. In the illustrated embodiment, the syringe assembly 100 extends between a proximal end 102 and a distal end 104. Further, the illustrated syringe assembly 100 includes a syringe barrel 110 having an interior surface 112. The interior surface 112 may define a reservoir 114. The reservoir 114 defined by interior surface 112 may be any suitable size and shape, e.g., for receiving a syringe plunger (such as plunger 120 discussed below). In one embodiment, the reservoir 114 may be generally cylindrical in shape. The reservoir 114 defined by interior surface 112 may be configured to receive a substance 15. Syringe barrel 110 may further include a tip 116 having an opening 117 in communication with the reservoir for receiving or expelling the substance 15 from the reservoir 114. In the illustrated embodiment, the tip 116 and opening 117 are disposed adjacent the distal end of the syringe barrel.

Syringe barrel 110 may include an additional opening 118 located, for example, at a proximal end of the barrel, for receiving a plunger 120, which may be disposed or partially disposed within the syringe barrel 110. The plunger 120 may comprise an elongate handle portion 122 having both a proximal end 124 and a distal end 126. The plunger 120 may typically have a length that is at least as long as a length of the syringe barrel 110. Accordingly, the proximal end 124 of the plunger may extend out from the barrel 110 when the plunger is disposed within the barrel 110. The plunger 120 may otherwise have any size and shape that is suitable for being disposed within the syringe barrel 110.

A plunger tip 130 may be coupled to handle portion 122. The plunger tip 130 may be a tip that is integrally molded with handle portion 122 or a tip that is attached separately. In one embodiment, the plunger tip 130 may be coupled to the distal end 126 of handle portion 122. The plunger tip 130 may comprise an external surface 134. In certain embodiments, the plunger tip 130 may be configured to contact at least a portion of the interior surface 112 of barrel 110. Accordingly, the plunger tip 130 may have a size and shape that is complimentary to the size and shape of the reservoir 114 defined by interior surface 112. For example, the plunger tip 130 may be generally cylindrical in shape such that a portion of its external surface 134 may have a circumference that is the same or similar in size to a circumference of the interior surface 112 of a barrel 110 that is also cylindrical in shape.

Furthermore, the plunger tip 130 may be sized such that, when disposed within the syringe barrel 110, the syringe barrel 110 radially constrains and/or compresses the plunger tip 130. The plunger tip 130 may be comprised of an elastomeric material that, due to the compression, provides a radially outward-oriented force on the interior surface 112 of the syringe barrel 110. Compression of the plunger tip 130 may thus result in a radial outward force that tends to seal the plunger tip 130 (including any covering 140 as discussed below) against the interior surface 112 of the syringe barrel 110.

In some embodiments, a covering 140 may be disposed on the external surface 134 of the plunger tip 130. In certain embodiments, covering 140 may be disposed on the entire external surface 134 of plunger tip 130. In other embodiments, covering 140 may be disposed on only a limited portion of the external surface 134 of the plunger tip 130. In certain embodiments, the covering 140 may be disposed on the external surface 134 such that it is positioned between at least a portion of the external surface 134 of the plunger tip 130 and the interior surface 112 of barrel 110. In such instances, the covering 140, rather than the exterior surface 134, will be in direct contact with the interior surface 112. The covering 140 may further be disposed on the external surface 134 of plunger tip 130 such that it is positioned between the external surface 134 and reservoir 114. In that way, the covering 140 may provide a barrier between the external surface 134 and a substance 15 loaded in the reservoir 114 such that there is no physical contact between the external surface 134 and substance 15.

The covering 140 may be compliant or flexible such that the covering 140 compresses and expands with the plunger tip 130. In some embodiments, the covering 140 may flex with the plunger tip 130 such that when the plunger tip 130 is compressed within the syringe barrel 110, the plunger tip exerts a force radially outward on the covering 140, causing the covering 140 to seal against the interior surface 112 of the syringe barrel 110. In some instances the plunger tip 130 may provide resiliency and/or compressibility to the plunger tip 130-covering 140 assembly while the covering 140 provides a friction bearing surface against the interior surface 112 of the barrel 110 and a contact surface for the substance 15 within the barrel 110.

FIGS. 2A-2B, 3A-3B, and 4A-4B are a series of views of various embodiments of a syringe assembly and components thereof that can, in certain respects, resemble a syringe assembly and components thereof described in connection with FIGS. 1A-1C. It will be appreciated that all the illustrated embodiments may have analogous features. Accordingly, like features are designated with like reference numerals, with the leading digits incremented to "2," "3," or "4." For instance, the covering is designated as "140" in FIGS. 1A-1C, and analogous coverings are designated as "240," "340," and "440," respectively, in FIGS. 2A-2B, 3A-3B, and 4A-4B. Relevant disclosure set forth above regarding similarly identified features thus may not be repeated hereafter. Moreover, specific features of the syringe assembly and related components (e.g., the covering) shown in FIGS. 1A-1C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the syringe assemblies and components thereof of FIGS. 2A-2B, 3A-3B, and 4A-4B. Any suitable combination of the features, and variations of the same, described with respect to the syringe assembly and components thereof illustrated in FIGS. 1A-1C can be employed with the syringe assemblies and components thereof of FIGS. 2A-2B, 3A-3B, and 4A-4B, and vice versa. This pattern of disclosure applies equally to further embodiments depicted in subsequent figures and described hereafter.

Figure 2A:
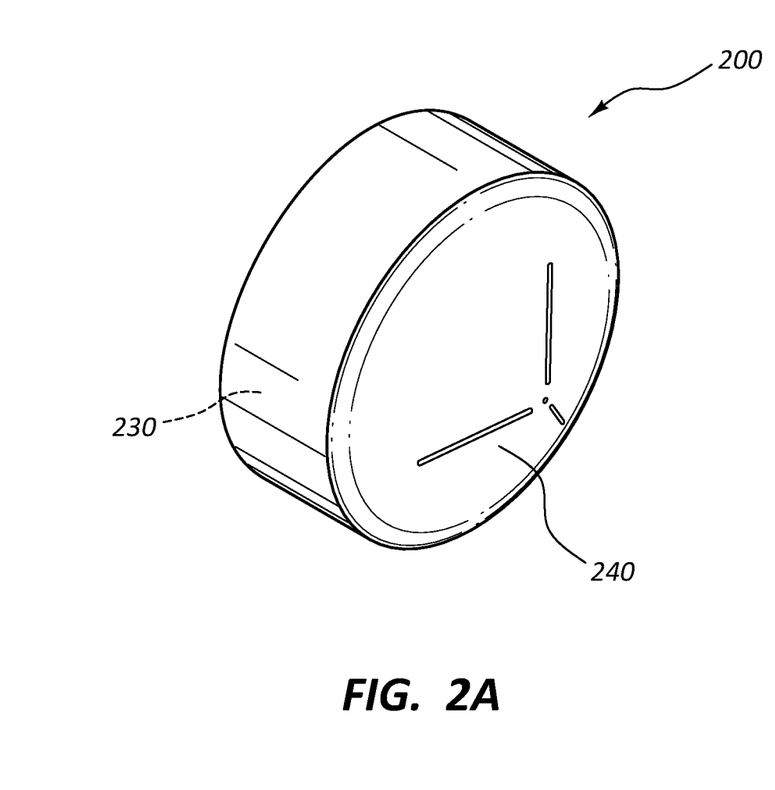
FIG. 2A illustrates a perspective view of an embodiment of a portion of a syringe assembly according to an embodiment of the present disclosure.
Figure 2B:
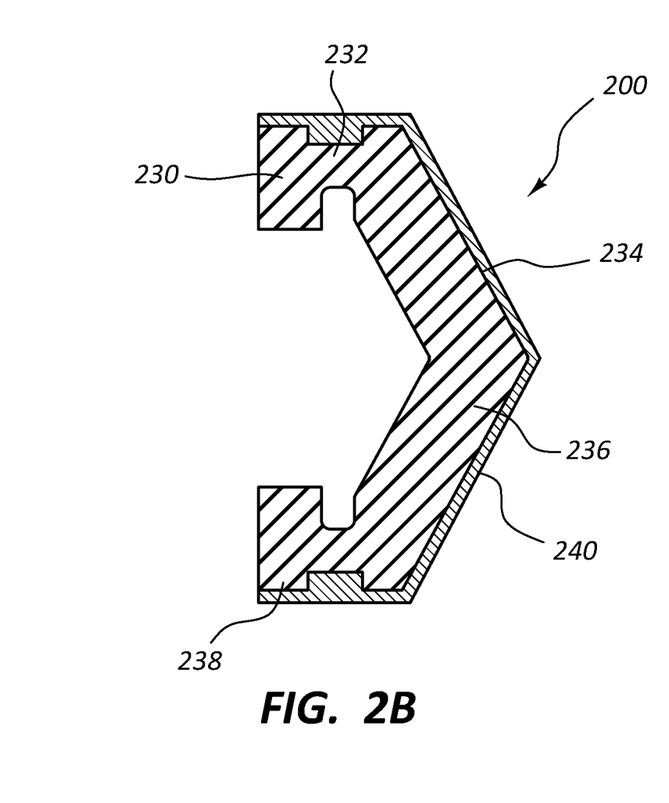
FIG. 2B illustrates a side cross-sectional view of the portion of the syringe assembly of FIG. 2A.

Referring to FIGS. 2A and 2B, a perspective view and a cross-sectional side view of a portion of the syringe assembly 100 is shown, as syringe tip subassembly 200. In the illustrated embodiment, syringe tip subassembly 200 includes a plunger tip 230 having an external surface 234. A covering 240 may be disposed on at least a portion of external surface 234.

Plunger tip 230 may include a sidewall 232 and a top portion 236 coupled to the sidewall 232. External surface 234 may cover all or portions of sidewall 232 and/or top portion 236. The sidewall 232 may include one or more ridges or detents 238 protruding from its external surface 234. These ridges or detents 238 may run along an entire circumference of external surface 234 of a circular sidewall, as is shown in the illustrated embodiment. Alternatively, the ridges or detents 238 may be spaced along such a circumference. Sidewall 232 and top portion 236 may comprise any suitable size and shape for a plunger tip. For example, sidewall 232 may comprise a generally cylindrical or circular shape, and top portion 236 may be, for example, flat or may extend outward from or inward toward sidewall 232.

Figure 3A:
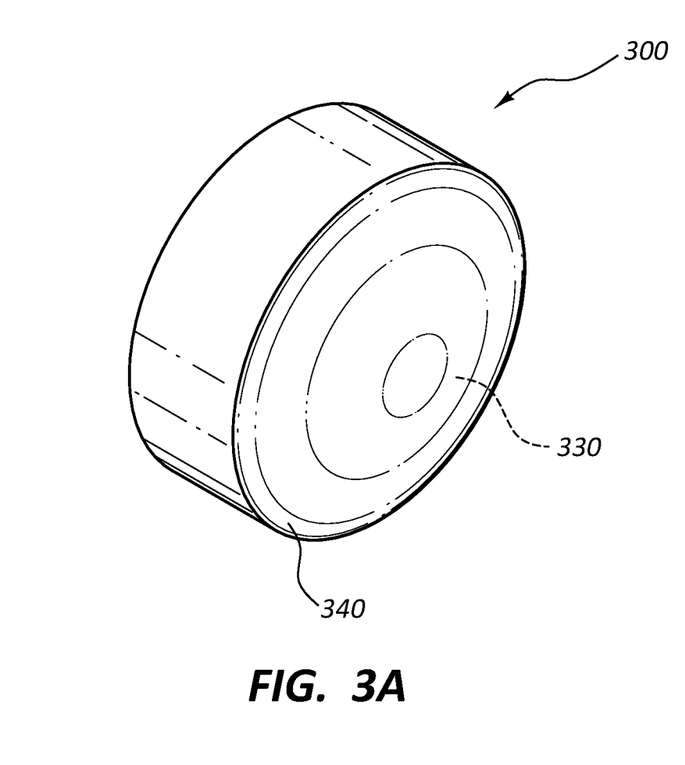
FIG. 3A illustrates a perspective view of an embodiment of a covering and a syringe plunger tip according to an embodiment of the present disclosure.
Figure 3B:
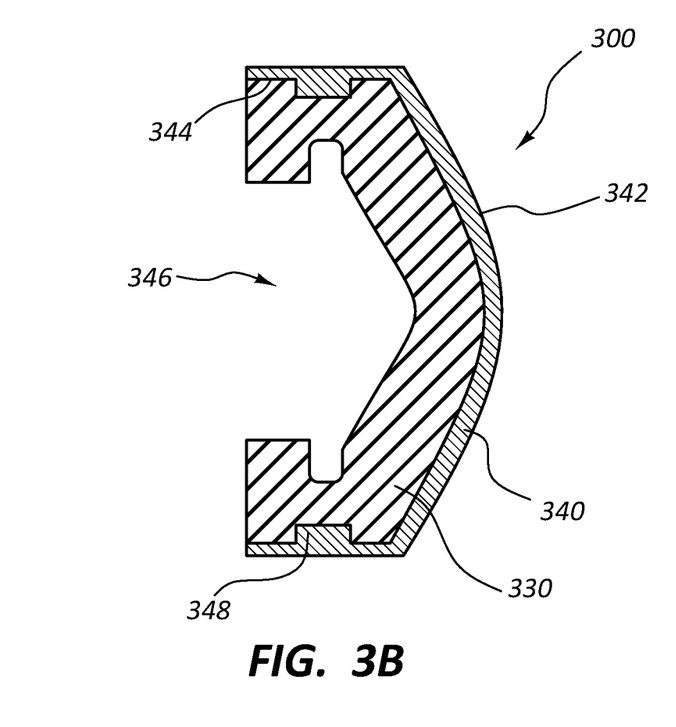
FIG. 3B illustrates a side cross-sectional view of the covering and the syringe plunger tip of FIG. 3A.

Referring to FIGS. 3A and 3B, a perspective view and a cross-sectional side view of another embodiment of a syringe tip subassembly 300 is shown. The syringe tip subassembly 300 comprises a covering 340 for a syringe plunger tip 330 according to the present disclosure. In the illustrated embodiment, syringe tip subassembly 300 may comprise a molded film. Covering 340 may include an outer surface 342 and an inner surface 344. The inner surface 344 may define a cavity 346 for receiving the plunger tip 330. Ridges or detents 348 may protrude from the inner surface 344 for engaging features of the plunger tip 330 and for holding the covering 340 in position on the plunger tip 330 via, for example, a friction fit.

Figure 4A:
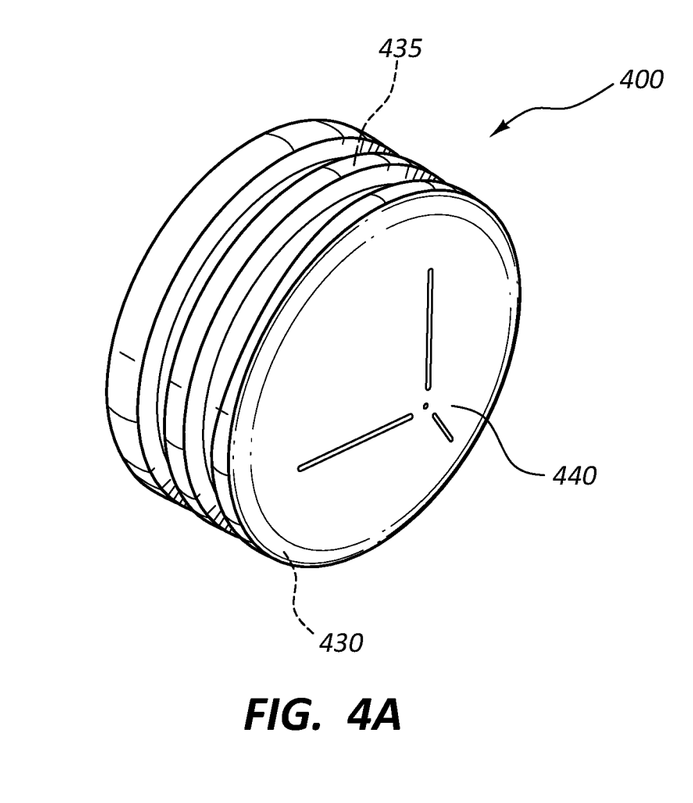
FIG. 4A illustrates a perspective view of an embodiment of a covering and a syringe plunger tip according to an embodiment of the present disclosure.
Figure 4B:
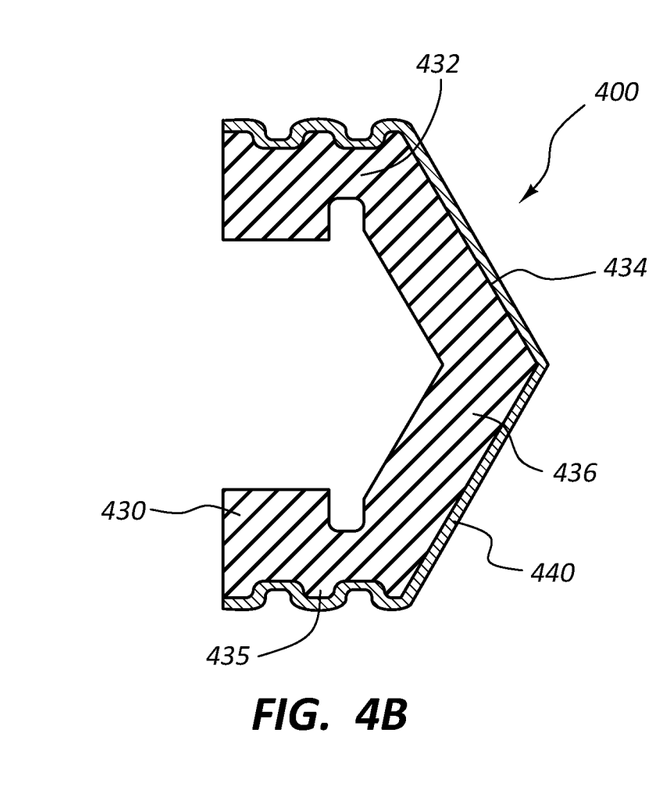
FIG. 4B illustrates a side cross-sectional view of the covering and the syringe plunger tip of FIG. 4A.

Referring to FIGS. 4A and 4B, a perspective view and a cross-sectional side view of another embodiment of a syringe tip subassembly 400 is shown. The syringe tip subassembly comprises a covering 440 for a syringe plunger tip 430 according to the present disclosure. Plunger tip 430 may comprise a sidewall 432, a top portion 436, and an external surface 434. In the illustrated embodiment, syringe tip subassembly 400 may comprise a film that may conform to an external surface 434 of plunger tip 430. In certain embodiments, the covering 440 may comprise a film that can be stretched and/or wrapped over the external surface 434. Accordingly, unlike other embodiments described herein, the covering 440 may not have a molded shape but rather may conform to and take on a shape of plunger tip 430 to which it is applied. The covering 440 may be held in place on the plunger tip 430 by, for example, frictional forces between the covering 440 and external surface 434 of plunger tip 430. In other embodiments, covering 440 may be held in place by, e.g., an adhesive.

In certain embodiments, plunger tip 430 may comprise one or more sealing rings 435. One or more sealing rings 435 may have a generally rounded shape and may protrude outward, for example, from external surface 434 of sidewall 432. In certain embodiments, sidewall 432 may have a generally circular shape, and the one or more sealing rings 435 may extend around an outer circumference of sidewall 432. Further, when covering 440 is applied to plunger tip 430, covering 440 may conform to the structure and/or shape of the one or more sealing rings 435, as is illustrated in FIGS. 4A and 4B.

The syringe barrel of any of the embodiments of the present disclosure may comprise any size, shape and material known in the art to be suitable for such syringe components. Accordingly, the syringe barrel may have a cylindrical shape and may be configured to have a plunger disposed within an interior reservoir of the syringe barrel. In some embodiments, the syringe barrel may comprise a plastic or polymeric material.

The handle portion of the plunger of any of the embodiments of the present disclosure may comprise any size, shape and material known in the art to be suitable for such syringe components. The handle portion may comprise a stiff or rigid material that can transfer a force exerted upon it to a plunger tip to which it is coupled or attached to move the plunger tip within the syringe barrel. In some embodiments, the handle portion may comprise a plastic or polymeric material. The handle portion may be longer in its length than in its width or diameter such that it can extend through the entire length of a syringe barrel. Such an elongate design allows the handle portion to be used to move a plunger tip throughout the entire length of a syringe barrel.

The plunger tip may be a tip that is integrally molded to the plunger handle portion or a tip that is attached separately. The plunger tip may be of any design that is of a suitable size and shape for being disposed or otherwise inserted into a syringe barrel such that the plunger tip is in mechanical communication with an interior surface of the syringe barrel. For example, the plunger tip may have a generally cylindrical or circular shape, and the syringe barrel may have a generally cylindrical or circular shape such that they are in contact with each other along all or a portion of an outer circumference of the plunger tip and an inner circumference of the syringe barrel. Further, the plunger tip may comprise an entirely solid structure or may comprise a structure that is hollow or includes a cavity.

In some embodiments, the plunger tip may comprise a material that is resiliently compressive such that the plunger tip may exert a force against the interior surface of the syringe barrel. Thus, the plunger tip may be capable of compressing and deforming against the interior surface of the syringe barrel when disposed within the interior of the syringe barrel. The force exerted by the resiliently compressive material deforming against the interior surface may serve to hold the plunger tip in position within the syringe barrel until displaced by a practitioner. The force may also be a sealing force that prevents any leakage or transmission past the plunger tip of a substance loaded within a reservoir defined by an interior surface of the syringe barrel. In some embodiments, the plunger tip may comprise a material containing silicon, such as, for example, silicone or silicone rubber.

Any of the components of the syringes disclosed herein (e.g., the barrel, plunger, handle portion and/or plunger tip) may comprise any polymeric material, such as, for example, acrylonitrile-butadiene-styrene polymer, polycarbonate, polypropylene, or cyclo-olefin polymer or copolymer. In some embodiments, any of the syringe components disclosed herein, including the plunger tip, may comprise a material that contains silicon, such as, for example, silicone or silicone rubber. Alternatively, any of the syringe components disclosed herein may comprise a silicon-free material. Additionally, any of the syringe components disclosed herein may be lubricated with a silicon-free lubricant.

The covering according to the present disclosure may comprise a material that is deposited onto the plunger tip by, for example, electrospinning or rotational spinning the material onto the plunger tip. In other embodiments, the covering may comprise a film of material that can be stretched and/or wrapped onto the plunger tip or a heat-shrink film that is applied to the plunger tip with application of heat. In some embodiments, the covering may comprise a molded film or molded material that is coupled to the plunger tip. Such a molded film or molded material may be coupled with an adhesive such as, for example, a chemical adhesive. The molded film or molded material may also be coupled to the plunger tip via a friction fit such that frictional forces between the molded film or molded material and the plunger tip retain the molded film or molded material in place on the plunger tip. The molded film or molded material may comprise ridges and/or detents disposed on and/or protruding from an interior surface of the molded film or molded material that engage with the plunger tip to increase the frictional forces holding the molded film or molded material in place.

The covering according to the present disclosure may comprise a different material than that of the plunger tip. In some embodiments, the material properties of the materials used for the covering and the plunger tip may differ in certain respects. Accordingly, the covering may comprise any suitable material including those that provide a reduced-friction interface, as compared to the plunger tip material, between a plunger tip and an interior surface of a syringe barrel. Thus, the covering may comprise a material that provides a lower coefficient of friction between the covering and the interior surface of the syringe barrel than the coefficient of friction between the plunger tip and the interior surface of the syringe barrel.

Accordingly, in some embodiments the use of a covering as disclosed herein may reduce or eliminate the need to use a lubricant (e.g., a lubricant containing silicone) within the syringe assembly (e.g., within the syringe barrel), which, in turn, may prevent such a lubricant from contaminating or otherwise affecting a substance held within the syringe. For example, in some instances silicone lubricants may coat or otherwise interfere with the hyrdation of PVA or gelatin foams. Coverings used in place of silicone lubricant may therefore be configured for use with PVA or gelatin foams. Additionally or alternatively, in certain embodiments, a covering as disclosed herein may be used to achieve a specific breakaway force with respect to the movement of a plunger tip through a syringe barrel. This break away force may be between 0.5 lbf and 3 lbf, 1 lbf and 2 lbf, less than 3 lbf, less than 2 lbf, less than 1.5 lbf, or less than 1 lbf. In other embodiments, a covering as disclosed herein may configured such that coefficients of static and dynamic friction between the covering and a surface of the syringe assembly (e.g., the interior surface of the syringe barrel) are closely matched, for example within 5% of each other, which may facilitate smooth or even use of the syringe.

The covering of the present disclosure may also comprise a material that isolates a plunger tip from a substance loaded into a reservoir defined by an interior surface of a syringe barrel by preventing physical contact between the plunger tip and the substance. Thus, the covering may comprise a material that is impermeable to either the substance or to a material contained in the plunger tip. For example, the covering may prevent a silicon-containing material, such as silicone, of a plunger tip from contaminating a substance comprising PVA or gelatin foam loaded in the syringe.

In some embodiments, the covering may comprise one or more polymeric materials. For example, the covering may comprise LLDPE, HDPE, ePTFE, PTFE, or a composite of any of these materials. In certain embodiments, the plunger tip may comprise silicone and the covering disposed on the plunger tip may comprise LLDPE, HDPE, ePTFE, PTFE, or a composite of any of these materials.

Methods for manufacturing a syringe assembly are also provided by the present disclosure. Referring again to FIGS. 1A-1C, one embodiment of such a method may comprise coupling a covering 140 to a plunger tip 130. Such coupling may comprise depositing a material onto at least a portion of any external surface 134 of the plunger tip 130 such that the deposited material forms the covering 140. For example, the material may be deposited by electrospinning or rotational spinning the material onto the external surface 134 of plunger tip 130. In some embodiments, LLDPE, HDPE, PTFE, or other polymers may be electrospun or rotational spun onto a plunger tip 130 comprising, for example, silicone. In other embodiments, the material may be electrospun or rotational spun onto a collector, then disposed on the plunger tip 130.

In another embodiment, coupling the covering 140 to the plunger tip 130 may comprise stretching and/or wrapping a film of material onto at least a portion of an external surface 134 of plunger tip 130 such that the stretched and/or wrapped material forms the covering 140. In one embodiment the material may be a thin film of LLDPE, HDPE, ePTFE, PTFE, or a composite of any of these materials. The LLDPE, HDPE, ePTFE, PTFE, or a composite of any of these materials may be stretched and/or wrapped onto a plunger tip 130 comprising, for example, silicone. The film covering 140 may conform to the features of the plunger tip 130, including, for example, sealing rings or other features.

In another embodiment, coupling the covering 140 to the plunger tip 130 may comprise applying heat to a covering comprising a heat-shrink material such that the heat-shrink material conforms or adheres to at least a portion of an external surface 134 of plunger tip 130. In certain embodiments, the heat-shrink material may comprise LLDPE, HDPE, ePTFE, PTFE, or a composite of any of these materials. The heat-shrink LLDPE, HDPE, ePTFE, PTFE, or a composite of any of these materials may be coupled to a plunger tip 130 comprising, for example, silicone.

In another embodiment, coupling the covering 140 to the plunger tip 130 may comprise fitting a covering comprising a molded material or molded film over or onto at least a portion of an external surface 134 of plunger tip 130 such that the molded material engages the plunger tip 130 with a friction fit that holds the molded material in place. The molded material may comprise detents or ridges to engage with the external surface 134 and to enhance the friction fit by increasing the friction between the molded material and the plunger tip 130.

The methods disclosed may further comprise coupling the plunger tip 130 to a plunger 120. In certain embodiments, the plunger tip 130 may be coupled to a distal end 126 of a handle portion 122 of a plunger 120. The methods may also comprise loading a substance 15 into the reservoir 114. The substance 15 may be loaded, e.g., through an opening 117 of a tip 116 of the syringe barrel 110 that is in communication with the reservoir 114. In some embodiments, the substance 15 may comprise PVA or gelatin foam, the plunger tip 130 may comprise silicone, and the covering 140 may comprise LLDPE, HDPE, ePTFE, PTFE, or a composite of any of these materials.

Methods for isolating a substance loaded in a syringe from one or more syringe components are also provided by the present disclosure. Such methods may prevent a syringe component from contaminating or otherwise contacting or interfering with the substance, and vice versa. Referring to FIGS. 1A-1C, one embodiment of such a method involves isolating a substance 15 from a syringe plunger tip 130. The methods may include coupling a covering 140 to an external surface 134 of a syringe plunger tip 130. The covering 140 may be coupled via any of the coupling methods described herein. The methods may further include disposing the coupled covering 140 and plunger tip 130 within a reservoir 114 defined by an interior surface 112 of a syringe barrel 110. The covering 140 and plunger tip 130 may be disposed by, for example, inserting them into the reservoir 114 through an opening 118 in syringe barrel 110. The methods may further comprise loading the reservoir 114 with a substance 15. The substance may be loaded in the reservoir 114, e.g., through an opening 117 in a tip 116 of the syringe barrel 110 that is in communication with the reservoir 114.

When plunger tip 130 and coupled covering 140 are disposed in the reservoir 114, and substance 15 is loaded in the reservoir 114, covering 140 may provide a barrier between the plunger tip 130 and the substance 15. In such a case, covering 140 isolates the substance 15 from plunger tip 130 by preventing physical contact between the plunger tip 130 and the substance 15. In addition, when disposed in the reservoir 114 as described, covering 140 may isolate the substance from other syringe components as well (e.g., a plunger 120). In some embodiments, the substance may comprise PVA or gelatin foam, the plunger tip 130 may comprise silicone, and the covering 140 may comprise LLDPE, HDPE, ePTFE, PTFE, or a composite of any of these materials.

In any of the foregoing embodiments, the syringe assembly and components thereof may be sterilization compatible materials. "Sterilization compatible materials," as used herein, refers to materials capable of being sterilized without rendering the materials unsuitable for their intended purposes. If a material is configured for sterilization by at least one method of sterilization without being rendered unsuitable for its intended purpose, then the material is a "sterilization compatible material." For example, a polymeric barrel may deform when autoclaved at temperatures sufficient to sterilize the barrel, rendering the barrel unsuitable for its intended purpose of maintaining a seal with a cylindrical or circular plunger. However, if the same polymeric barrel may be sterilized by another sterilization technique, such as irradiation, and maintain suitability for its intended purpose, then the polymeric material is a "sterilization compatible material."

In any of the foregoing embodiments, the syringe assembly and components thereof may be made from irradiation compatible materials. "Irradiation compatible materials," as used herein, refers specifically to materials capable of being sterilized by irradiation without rendering the materials unsuitable for their intended purposes. For example, a plunger or interior surface of a barrel may comprise a material or lubricant that upon irradiation changes in physical properties such that the syringe is unsuitable for its intended purpose. For example, irradiation may alter certain materials or lubricants such that a syringe using those materials would have an unacceptably high initial peak force required to start movement of the plunger. Or, in another example, irradiation may alter certain materials or lubricants such that a syringe using those materials would have an unacceptably non-uniform force required for travel of the plunger over the length of the barrel or an unacceptably high force required for travel of the plunger over the length of the barrel.

The covering, syringe plunger tip, and other components disclosed herein may be used with a syringe loaded with any suitable substance for loading into a syringe. In certain embodiments, the syringe may be loaded with a substance comprising an embolic agent comprising a microparticle and/or microsphere. Examples of microparticles include polyvinyl alcohol (PVA) microparticles. Examples of microspheres include trisacryl cross-linked with gelatin microspheres, sodium acrylate vinyl alcohol copolymer microspheres, and polyvinyl alcohol based hydrogels.

While specific embodiments of coverings for syringe plunger tips and methods related thereto have been described, it is to be understood that the disclosure provided is not limited to the precise configuration and components disclosed. Various modifications, changes, and variations apparent to those of skill in the art having the benefit of this disclosure may be made in the arrangement, operation, and details of the devices, methods, and systems disclosed, with the aid of the present disclosure.

Furthermore, any reference to "one embodiment," "an embodiment," or "the embodiment," as used throughout this disclosure, means that a particular feature, structure, or characteristic described in connection with that embodiment is included in at least one embodiment. Thus, the quoted phrases, or variations thereof, as recited throughout this specification are not necessarily all referring to the same embodiment.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A syringe comprising:
   a barrel comprising an interior surface defining a reservoir having a proximal-most end and a distal-most end;
   a plunger comprising:
      an elongate handle portion defining a proximal end and a distal end; and
      a plunger tip coupled to the distal end of the elongate handle portion when the plunger tip is disposed at the proximal-most end and the distal-most end of the reservoir, the plunger tip comprising:
         a first material,
         an annular wall, and
         a top portion coupled to the annular wall; and
      a covering at least partially disposed on an external surface of the plunger tip, the covering comprising a second material,
   wherein at least one material property of the first material differs from at least one material property of the second material,
   wherein the covering is disposed between an entire external surface of the annular wall of the plunger tip and the interior surface, and
   wherein the covering is disposed between an internal cavity surface of the plunger tip and the distal end of the elongate handle portion, wherein the internal cavity surface is a proximal facing surface.

2. The syringe of claim 1, wherein the second material comprises linear low-density polyethylene (LLDPE).

3. The syringe of claim 1, wherein a coefficient of friction between the second material and the interior surface is lower than a coefficient of friction between the first material and the interior surface.

4. The syringe of claim 1, wherein the covering is configured to isolate the plunger tip from a substance loaded in the reservoir by preventing physical contact between the plunger tip and the substance.

5. The syringe of claim 4, wherein the plunger tip comprises silicone and the covering is configured to isolate the silicone from at least one of polyvinyl alcohol (PVA) or gelatin foam.

6. The syringe of claim 1, wherein the plunger tip comprises a resiliently compressible material configured to provide a sealing force on the interior surface of the barrel.

7. The syringe of claim 6, wherein the covering is configured to flex with the plunger tip such that the sealing force is transmitted through the covering to the interior surface.

8. The syringe of claim 1, wherein the covering comprises a molded material configured to retain its shape.

9. The syringe of claim 8, wherein the covering further comprises one or more mating features configured to engage with the plunger tip in a friction fit.

* * * * *